United States Patent [19]
Thomas et al.

[11] Patent Number: 5,522,901
[45] Date of Patent: Jun. 4, 1996

[54] IMPLANT FOR REPLACING A REAR PATELLA PART

[75] Inventors: Wolfram Thomas, Rome, Italy; Martin Schug, Stockelsdorf, Germany

[73] Assignee: Eska Implants GmbH, Lubeck, Germany

[21] Appl. No.: 78,703

[22] Filed: Jun. 16, 1993

[30] Foreign Application Priority Data

Jun. 26, 1992 [DE] Germany ............... 42 21 006.2

[51] Int. Cl.⁶ ................ A61F 2/30; A61F 2/38
[52] U.S. Cl. ......................... 623/20; 623/18
[58] Field of Search ................. 623/16, 18, 20

[56] References Cited

U.S. PATENT DOCUMENTS

| | | | |
|---|---|---|---|
| 4,808,185 | 2/1989 | Penenberg et al. | 623/20 |
| 4,997,445 | 3/1991 | Hodorek | 623/16 |
| 5,019,104 | 5/1991 | Whiteside et al. | 623/20 |
| 5,236,462 | 8/1993 | Mikhail | 623/20 |

FOREIGN PATENT DOCUMENTS

| | | | |
|---|---|---|---|
| 0307654 | 3/1989 | European Pat. Off. | A61F 2/38 |
| 2682590 | 4/1993 | France | A61F 2/38 |
| WO91/15168 | 10/1991 | WIPO | A61F 2/38 |

*Primary Examiner*—Debra S. Brittingham
*Attorney, Agent, or Firm*—Panitch Schwarze Jacobs & Nadel

[57] ABSTRACT

An implant to replace a rear patella part is provided, which comprises a prosthesis part imitating the patella part and a metal attachment part fixed in the prosthesis part, with which the implant can be attached in the natural patella part. In order to produce a gentle and secure attachment for the implant, the attachment part has a convexly curved external contour, which at least in sections has an open-cell and open-pore surface structure.

12 Claims, 2 Drawing Sheets ured patella, which is used to attach the peg, considerably
IMPLANT FOR REPLACING A REAR PATELLA PART The invention relates to an implant for replacing a rear patella part, having a prosthesis part made from plastic or ceramic material imitating the patella part, and having a metal attachment part fixed in the prosthesis part for fastening the implant in the natural patella.

Such an implant is known, for example, from EP A2-0 307 654, in which the prosthesis part is attached in a positive and non-positive manner by means of a peg in the natural patella. A problem with this is that the bore made in the natural patella, which is used to attach the peg, considerably weakens the osseous structure and also destroys blood vessels in the centre of the patella, which are indispensable for the vital supply of the patella. Consequently, there is the danger of a premature loosening of the patella partial replacement as a result of necrosis occurring.

The object of the invention is therefore to develop further the implant of the aforementioned type so that a stable attachment, which is gentle to the tissue, is achieved in the natural patella.

This object is achieved according to the invention with the implant of the aforementioned type in that the attachment part possesses a convexly curved external contour, which at least in sections has an open-cell and open-pore surface structure.

The advantages of the invention lie in particular in the fact that the convexly curved external contours are attached in a recess in the patella interior, which is curved in corresponding manner over a wide area, as a result of which the provision of one or more bores in the patella bone and the resultant local weakening of the osseous tissue can be avoided and at the same time the blood and nerve vessel connections are retained to a very great extent. The open-pore or open-cell surface structure provided over a wide surface on the external contours of the attachment part furthermore results in that the adjacent natural osseous tissue can grow into the open cells or pores, as a result of which the bone/implant unit experiences a considerable increase in strength. By the convex external contours of the attachment side, an adaptation to the anatomical structures of patella bone, and consequently a particularly effective ingrowth of the osseous tissue into the open cells of the attachment part is achieved. Furthermore a positive fit over a large area is produced, which in particular improves the primary stability after implantation, if the implanted patella is forced against the patella bearing surface of a knee joint endoprosthesis under a bearing pressure which is determined by the natural ligaments and tendons.

According to a particularly preferred embodiment of the invention, the contact face of the prosthesis part, which comes to abut against the resection face of the natural patella, is only slightly smaller than the natural resection face, and the attachment part, which is attached centrally in the contact face of the prosthesis part, occupies a relatively large part of the contact face. The external contour of the attachment part advantageously preferably has substantially the shape of a spherical segment with a comparatively large spherical radius, partly with opposed radial symmetry, so that the convex curvature of the external contours is slight, and consequently the depth of the corresponding recess in the patella is also slight, in order to weaken the strength of the natural remaining patella part as little as possible, and in order not to alter the natural function thickness of the patella.

In a particularly preferred manner the attachment part is provided over its entire free surface with an open-cell or open-pore surface structure, in order to provide the adjacent osseous tissue with the greatest possible contact surface.

Between the attachment part and the prosthesis part is preferably provided at least one projection and a corresponding recess, e.g. to produce a conical plug-in type connection. Alternatively the prosthesis part can be shrunk and injected onto one or more projections on the attachment part, in order to produce a secure bond between the attachment part and the prosthesis part.

In a particularly preferred manner the projection has a circular or cylindrical construction and extends substantially right to the periphery of the attachment part and, for example, on its peripheral surface, bears an external thread, which can be screwed into a correspondingly threaded bore in the prosthesis part. Alternatively between the attachment part and the prosthesis part can be provided a twist or snap connection, which in addition may also be disposed for injection moulding or shrinking on further attachment elements.

According to a further preferred embodiment of the invention, the prosthesis part has a central projection, which engages in a corresponding recess in the attachment part. In a particularly preferred manner the central projection and the corresponding recess can be constructed as a conical plug-in type connection, whereby for this purpose the projection of the recess accordingly tapers conically. In this embodiment of the invention firstly between the attachment part and the prosthesis part a particularly simple and reliable connection is projected, which furthermore can also be released. Should the prosthesis part be subject to particular wear, with this embodiment it is possible to change just the prosthesis part, while the osseous ingrown attachment part can remain on the patella. Surgical intervention with such a revision is as a result less serious, and the patella part is not further reduced during a revision.

In a particularly preferred manner between the central projection of the prosthesis part and the corresponding recess there may also be provided means which produce a snap connection and as a result secure the conical plug-in type connection between the prosthesis part and the attachment part.

In a particularly preferred manner at the foot of its central projection the prosthesis part has a circular depression, the depth of which gradually decreases in the radially outward direction, and which contains a corresponding torus of the attachment part. By this design of the boundary face between the prosthesis part and the attachment part an almost uniform wall thickness of the prosthesis part is achieved without sharp-edged bearing surfaces to the attachment part.

The attachment part preferably possesses a radially outwardly directed plane peripheral flange, which comprises a smooth, i.e. unstructured, surface, which firstly lies on a plane, radial peripheral edge of the prosthesis part, and secondly abuts the resection face of the patella and ensures that direct contact is avoided between the prosthesis part made from plastic or ceramics and the natural bone.

In order to increase the primary rotational stability after implantation, pointed spike protrusions are advantageously provided on the peripheral flange of the attachment part, and are directed towards the resection surface and during the operation penetrate into the natural patella and as a result connect the implant in a rotationally secure manner to the patella.

Advantageous refinements of the invention are characterised by the features of the subordinate claims.

Exemplified embodiments of the invention are explained in further detail below with reference to the drawings.

Figure 1:
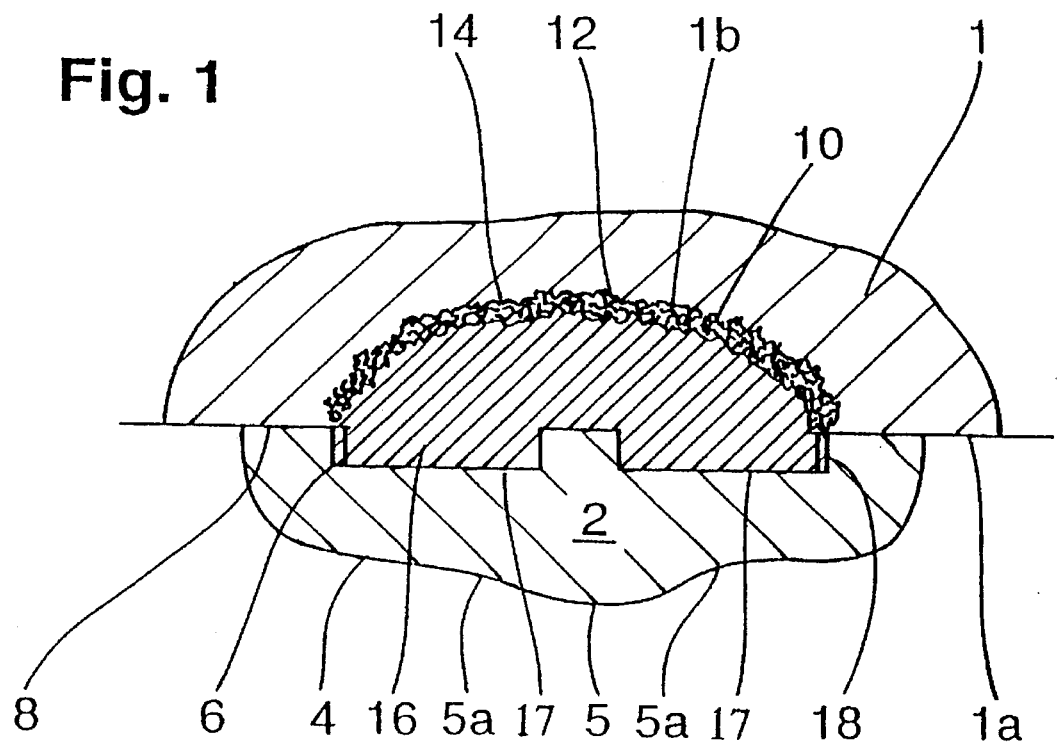
FIG. 1 shows a cross section through a first embodiment of the invention.

As shown in FIG. 1, from a patella having a plane resection surface 1a the rear patella part is resected. Therefore in FIG. 1 only the front natural remaining patella part 1 is shown, which at the rear is limited by the resection surface 1a. In the centre the resection surface 1a comprises a substantially spherical depression 1b, in which the implant is attached in the natural osseous tissue.

The implant contains a prosthesis part 2 made from plastic or ceramic material which imitates the resected patella part and which towards the natural patella 1 is limited by a plane contact surface 8, which during the insertion of the implant comes to abut the resection surface 1a. The plane contact surface 8 has a size which is preferably slightly smaller than the resection surface 1a of the remaining patella part 1. The prosthesis part 2 has a rear slide face 4, which comes to abut the condyle outer face of one of the known knee joint endoprostheses.

The implant also comprises an attachment part 10, which can be attached by means of a cylindrical or annular projection 16 in a corresponding recess 17 in the contact surface 8 of prosthesis part 2. For this purpose on the shell face of the projection 16 is provided an external thread 18, which can be screwed into the internal thread of a corresponding thread bore 6 in prosthesis part 2.

The attachment part 10 possesses—directed away from the prosthesis part 2—a convexly curved external contour 12 the attachment part 10 is provided with an open-cell or open-pore surface structure 14, into which the adjacent osseous tissue can grow. The diameter of the cylindrical or circular projection 16 should be as large as possible, i.e. only slightly smaller than the external periphery of the prosthesis part 2, in order to ensure an adequate fastening of the attachment part 10 in the prosthesis part 2.

Instead of the screw connection between the attachment part 10 and prosthesis part 2, if the prosthesis part is made out of plastic, projections on the attachment part can be injected and respectively the prosthesis part 2 can than be shrunk onto corresponding projections or be attached by means of a snap or twist connection.

On its free surface 4 remote from the attachment part 10 the prosthesis part 2 comprises a longitudinal bead 5, and adjacent thereto lateral surfaces 5a extending concavely on both sides. The free surface 4 of the prosthesis part 2 is as a result constructed so that a congruent contact is produced with respect to the femur articular surfaces, as a result of which an optimised introduction force is produced, which is accompanied by gentle treatment of the prosthesis part.

Figure 2:
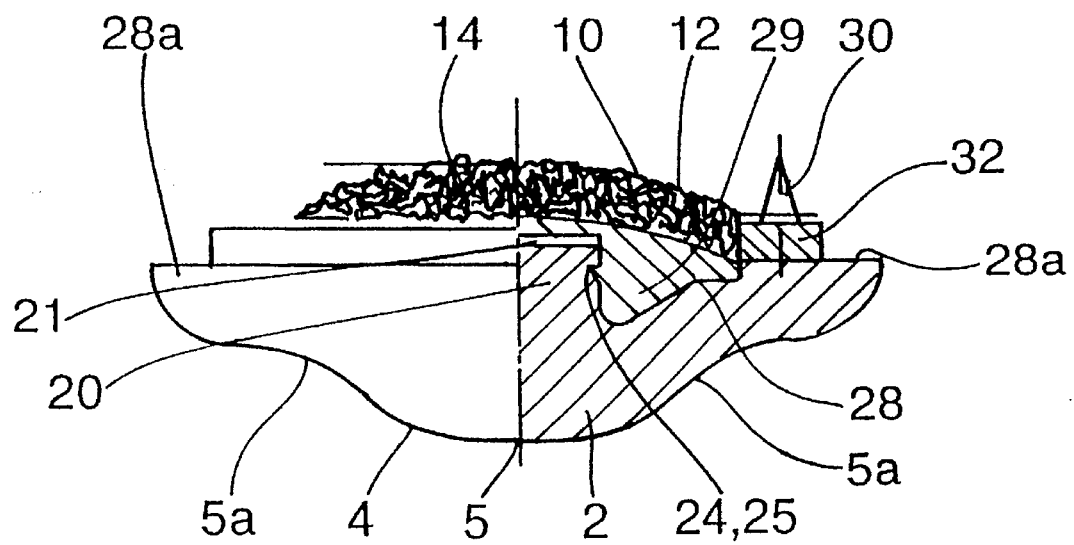
FIG. 2 shows a cross section through a second embodiment of the invention.
Figure 3:
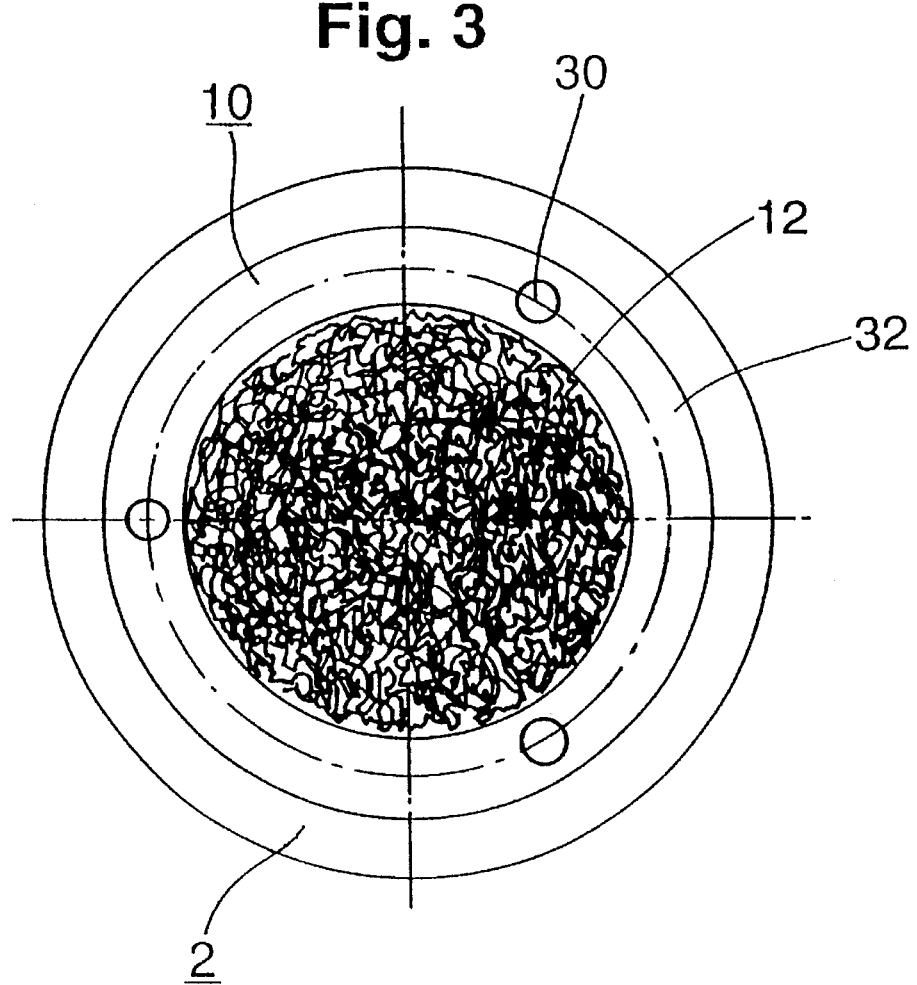
FIG. 3 shows a plan view of the implant of FIG. 2, seen from below.

In FIGS. 2 and 3 is represented a cross section and a plan view of a further embodiment of the implant, in which the natural patella is omitted. The prosthesis part 2 possesses a central projection 20, which is orientated towards the attachment part 10 and protrudes into a corresponding recess 21 in the prosthesis part tapers inwardly in a corresponding manner, so that the projection 20 and recess 21 form a conical plug-in type connection. Between the projection 20 and the recess 21 are provided means, e.g. a peripheral groove 24 and a corresponding peripheral bead 25, which engage in one another when the attachment part and the prosthesis part are connected to one another and represent a snap connection.

At the base of the central projection 20 of the prosthesis part 2 is provided an annular depression 28, the depth of which decreases in the radially outward direction. In the radially outward direction a plane peripheral edge 28a is joined to the depression 28. The recess 21 in the attachment part 10 passes in the radially outward direction into a corresponding torus 29, which fills the depression 28 of prosthesis part 2. On its peripheral edge the attachment part has a radially outwardly directed plane peripheral flange, which has a smooth surface on both sides and firstly lies on the radial peripheral edge 28a of the prosthesis part 2, and secondly abuts against the resection surface 1a of the patella and prevents the prosthesis part coming into direct contact with the patella bone. To the peripheral flange 32 are attached pointed spiked protrusions 30 directed towards the patella, which during implantation penetrate the patella bone and produce primary rotational stability. On the attachment side attachment part 10 has—as does the embodiment according to FIG. 1—a convexly curved external contour 12, which has an open-cell or open-pore surface structure 12. On the free surface 4 remote from the attachment part 10, prosthesis part 2 has a longitudinal bead 5 and adjacent thereto lateral surfaces 5a extending concavely on both sides.

We claim:

1. An implant for the replacement of a rear patella part, having a prosthesis part made from a non-metallic material imitating the rear patella part and having a metal attachment part fixed in the prosthesis part for fixing the implant in the natural patella part, wherein the metal attachment part has a convexly curved external contour, which at least in sections has an open-cell and open-pore surface structure, wherein the metal attachment part and the prosthesis part are connected by means of at least one projection and a corresponding recess which engage in one another and the projection is seated on the attachment part and bears an external thread which can be screwed into a corresponding threaded bore in the prosthesis part.

2. An implant according to claim 1, wherein the external contour of the attachment part substantially has the form of a spherical segment.

3. An implant according to claim 1, wherein over an exposed surface the attachment part has a porous surface structure.

4. An implant according to claim 1, wherein the prosthesis part is shrunk onto at least one projection on the attachment part.

5. An implant according to claim 1, wherein the prosthesis part is made from plastic material injected onto the attachment part.

6. An implant according to claim 1, wherein the attachment part and the prosthesis part are connected by means of at least one projection and a corresponding recess which engage in one another, and the projection and the corresponding recess have an annular shape.

7. An implant according to claims 1, wherein the attachment part forms a twist or snap connection with the prosthesis part.

8. An implant according to claim 1, wherein between the prosthesis part and the attachment part is provided a conical plug-in type connection.

9. An implant according to claim 1 wherein the implant is provided with several pointed spiked protrusions directed towards the resection surface of the patella.

10. An implant to claim 9, wherein the spiked protrusions are disposed radially outside the convexly curved external contours of the attachment part.

11. An implant according to claim 1, wherein the attachment part has a radially outwardly directed plane peripheral flange having a smooth surface, which lies on a plane, radial peripheral edge of the prosthesis part, and abuts the resection surface of the patella.

12. An implant according to claim 1, wherein on its free surface remote from the attachment part, the prosthesis part comprises a longitudinal bead and adjacent thereto lateral surfaces extending concavely on both sides.

\* \* \* \* \*